United States Patent [19]

Reed et al.

[11] 4,002,174
[45] Jan. 11, 1977

[54] AIR EMBOLUS ASPIRATOR

[75] Inventors: Charles C. Reed; Denton A. Cooley, both of Houston; Russell G. Sharp, Sugar Land, all of Tex.

[73] Assignee: Texas Medical Products, Inc., Houston, Tex.

[22] Filed: Oct. 14, 1975

[21] Appl. No.: 621,922

[52] U.S. Cl. .................. 128/347; 128/214 R; 128/221; 128/276

[51] Int. Cl.² ............ A61B 17/34; A61M 1/00

[58] Field of Search .......... 128/214 R, 214.2, 221, 128/215, 276–278, 347

[56] References Cited

UNITED STATES PATENTS

| 1,503,399 | 7/1924 | Webb | 128/221 |
|---|---|---|---|
| 3,776,239 | 12/1973 | Cooley | 128/347 |
| 3,913,577 | 10/1975 | Nehra et al. | 128/276 |
| 3,957,048 | 5/1976 | Jacobs | 128/214 R |

FOREIGN PATENTS OR APPLICATIONS

| 1,566,203 | 3/1969 | France | 128/214.2 |
| 1,082,041 | 6/1954 | France | 128/221 |
| 483,499 | 7/1953 | Italy | 128/221 |

OTHER PUBLICATIONS

Groves et al — Jour. Thorac. & Card. Surg., vol. 47 No. 3, Mar. 1964, pp. 349–355.

*Primary Examiner*—Dalton L. Truluck
*Attorney, Agent, or Firm*—H. Ross Workman; J. Winslow Young

[57] ABSTRACT

A device for aspirating air emboli from a blood vessel (e.g. the aorta during open-heart surgery), the aspirating device having a hollow cannula with radially spaced openings for aspirating air and bending angularly midlength to permit aspiration of air emboli while maintaining the device generally flat against the exposed patient surface. A hub comprising part of the device is constructed to provide a dual coupling presenting both male and female attachment sites.

5 Claims, 3 Drawing Figures

AIR EMBOLUS ASPIRATOR

BACKGROUND

1. Field of the Invention

The invention relates to cannulas and more particularly to a specialized cannula construction for aspirating air emboli from blood vessels.

2. The Prior Art

Entrapment of air in the left side of the heart is one of the great hazards of open-heart surgery due to the probability that the entrapped air will enter the systemic circulation. Conventionally, most open-heart surgery is conducted either through a sternal splitting incision with the patient supine or through a right anterolateral sub-mammary incision with the patient's right side elevated approximately 30° from the horizontal. In both of these positions the highest point in the central cardiovascular system is the ascending aortic arch between the aortic valve ring and the innominate artery takeoff.

In many patients, usually those undergoing mitral valve surgery, the physician will work through the left atrium with the heart beating, the aortic valve acting as a dam to maintain an empty left heart. The perfusion pressure keeps the aortic valve closed and minimizes the amount of air which enters the aortic route from the left ventricle. It has been found, however, that even the simplest digital manipulation of the mitral valve may trap air in the left ventricle and, if the ventricle is still beating, the next contraction will expel this air through the aortic valve into the aorta. The air will then collect in the aorta at its highest point. The air, in the form of a bubble is characterized as an air embolus. Under normal circulatory dynamics, aortic flow would certainly sweep such air embolus into the innominate artery and thereby enter the intracranial circulation. The serious adverse effects of this damaging air embolus are well known. If the air embolus is comparatively large and gains access to the right carotid artery, serious neurologic defects in the left half of the patient's body will likely result.

It has been discovered, however, that during the use of a cardiac bypass machine, when the heart is open, there is no return of blood through the vena cava and little or no forward motion of the blood through the aortic valve. Hence, the air embolus, at this point in the surgical procedure, is imprisoned in the aortic arch.

In order to alleviate the serious risk of a disabling air embolus when the heart is returned to normal function, it is known to suture in place a vent in the highest portion of the aortic arch during surgery. See, for example, Groves and Effler, 47 J. Thoracic and Cardiovas. Surg. No. 3, March, 1964, page 349, et. seq.

The mentioned vent structure and related prior art devices are seriously deficient in that they merely provide a communication between the aorta and the exterior of the blood vessel permitting blood and gases to continuously flow out of the vent. The presence of blood flowing from the aorta tends to obscure the surgical field and complicate the physician's work. It is also known to utilize a conventional needle or the like connected to a vacuum which is then penetrated into the aorta in an effort to aspirate the air embolus. Conventional needles have proved to be cumbersome and difficult to use. For example, it has been found extremely difficult to appropriately penetrate the aorta so as to assure that the aspirating tip of the needle is in direct contact with the air embolus. If the needle travels too far through the embolus, only blood will be aspirated. If the needle is adjacent the air embolus, but the aspirating bevel of the needle facing away from the embolus, the embolus will not be aspirated. Furthermore, because the prior art aspirating needle is attached to a suction line, the natural weight of the suction line tends to force the needle out of the vertical penetration position and cause the needle to lie flat against the inside of the aorta. Not only does this position frequently remove the aspirating tip of the needle away from the air embolus, it maximizes the likelihood of inadvertent movement of the needle relative to the aorta risking laceration of the aorta or at least bringing undesirable tissue damage to the blood vessel.

Accordingly, it would be a significant contribution to the art to provide an air embolus aspirating device having maximum surface area in contact with the air embolism for aspiration purposes, which is configurated to lie flat against the aorta or other patient surface during the course of aspiration and which will easily couple with existing vacuum lines and/or fluid delivery circuits for versatile aspiration of air emboli from the blood vessel. Such a device is disclosed and claimed herein.

BRIEF SUMMARY AND OBJECTS OF THE INVENTION

The present invention provides an improved aspiration needle which, at the trailing end, is provided with a dual coupling capacity for attachment to a straight suction tube or to a luer coupling. The leading end of the aspirator comprises a penetrating member which is perforated at radially spaced locations to maximize contact with air emboli upon penetration. Notably, the penetrating member is oriented angularly with respect to the body of the aspirator so as to facilitate penetration and minimize inadvertent laceration of the blood vessel.

Accordingly, it is a primary object of the present invention to provide an improved aspirator for air emboli.

It is another valuable object of the present invention to provide an aspirator having a penetrating tip which is configurated to penetrate directly into a blood vessel while at the same time permitting associated suction tubing to lie essentially flat against the penetrated surface.

Another valuable object of the present invention is to provide an air emboli aspirator which is safe and efficient for use in blood vessels.

These and other objects and features of the present invention will become more fully apparent from the following description and appended claims taken in conjunction with the accompanying drawing.

DETAILED DESCRIPTION OF THE PREFERRED EMBODIMENT

Reference is now made to the drawings wherein like parts are designated with like numerals throughout.

Figure 1:
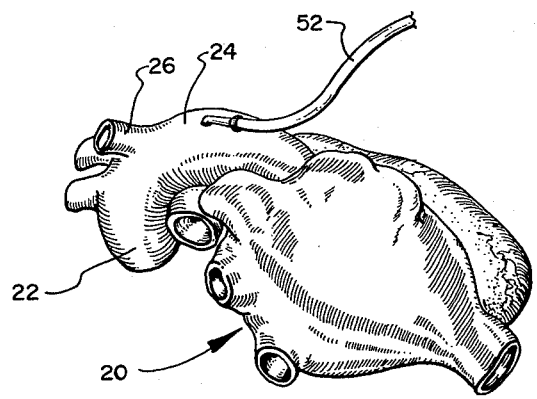
FIG. 1 is a schematic perspective view of a human heart oriented so as to reveal the ascending aorta with the presently preferred embodiment of the invention operably associated therewith.

It is understood that the air embolus aspirator of the present invention may be used in a variety of locations and circumstances. However, the most significant use presently contemplated deals with removing air emboli from the aorta during open-heart surgery. Accordingly, the use of the illustrated embodiment will be described in connection with the open-heart surgical procedure. With reference to FIG. 1, a human heart generally designated 20 is illustrated. The heart 20 is oriented so as to particularly reveal the aorta 22 with the ascending aortic arch 24 being situated at the top of the drawing. The innominate artery 26 and the aortic valve ring (not shown) define the usual area in which air emboli are trapped in the aortic arch 24 during surgery.

Figure 2:
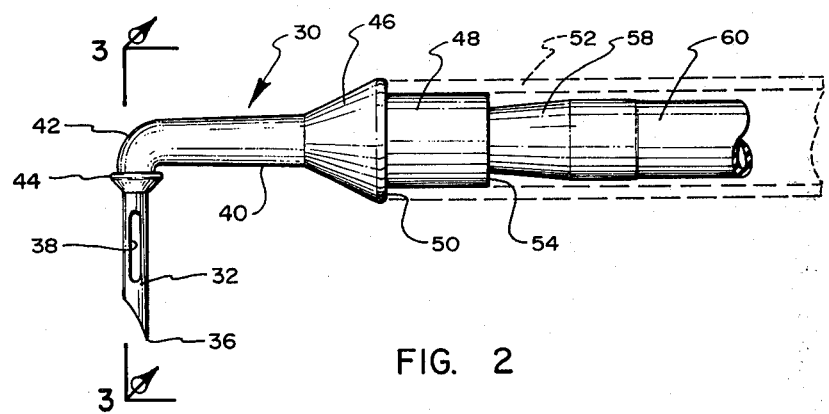
FIG. 2 is a side elevational view of the embodiment of FIG. 1, conventional suction tubing to be used therewith being shown in broken lines.
Figure 3:
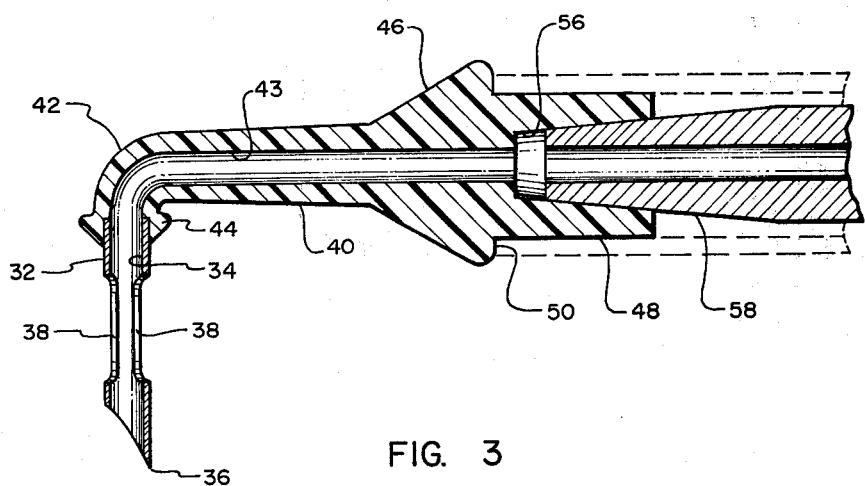
FIG. 3 is a fragmentary cross section taken along lines 3—3 of FIG. 2.

The aspirator for removing the air emboli can be best understood by reference to FIGS. 2 and 3. With particular reference to FIG. 2, the aspirator, generally designated 30, includes a leading end 32 or cannula which is preferably formed of metal needle stock. The leading end 32 had an interior hollow 34 (see FIG. 3) and a beveled tip 36 which is pointed to facilitate penetration of the aorta 24. The hollow 34 of the needle 32 opens at the bevel 36. In addition to the opening at bevel 36, the leading end 32 has a plurality of radially spaced elongated apertures 38 which extend a significant portion of the length of the leading end 32. The purpose of the apertures 38 is to maximize the exposure of any air emboli in the aorta 24 to the hollow 34 of the leading end 32. Other desirable aperture configurations giving access to air emboli at radially spaced locations could also be used. In the illustrated embodiment, there are three elongated apertures 38 equidistantly spaced radially about the periphery of the leading end 32. Clearly, any suitable number of apertures 38 could be used. Moreover, the apertures may be rotated in any suitable orientation which will maximize exposure of the apertures to air emboli in the aorta.

Another presently preferred embodiment found to be surprisingly successful in quickly aspirating air emboli includes the placement of an aperture 38 so as to be aligned with a plane passing through the longitudinal axis of the aspirator 30. This aperture orientation could best be observed if the leading end 32 illustrated in FIG. 2 were rotated 90° to the left so that aperture 38 opens directly to the left of FIG. 2.

The leading end 32 is mounted within the shank 40 of the aspirator 30. The shank 40 is preferably formed of a suitable plastic material such as polypropylene or nylon. In the embodiment of FIG. 2 the shank 40 is bent at 42 approximately 90° so that the leading end 32 is at essentially right angles with respect to the axis of the shank 40. The purpose of the bend 42 is to permit the shank 40 to rest upon the aorta 24 and to thus largely immobilize the leading end 32. Accordingly, there is substantially reduced likelihood that the aorta will be lacerated due to inadvertent movement of the shank 40 as will be hereinafter more fully described. While a 90° angular bend in the shank 40 is illustrated, any suitable bend angle accomplishing the aforementioned advantages could be used.

The shank 40 terminates in an annularly enlarged shoulder 44 which tapers away from the leading end 32. Significantly, the shoulder 44 further immobilizes the leading end 32 and renders the aspirator 30 more safe for use.

The shank 40 is continuous with an outwardly tapering intermediate portion 46 of hub 48. The hub 48 is cylindrical in configuration and has a diameter which is less than the largest diameter of the intermediate portion 46 so as to form a rearwardly facing shoulder 50. The hub 48 is sized so as to telescopically receive conventional suction tubing 52, shown in phantom lines in FIG. 2. The suction tubing 52 can be press-fit over the hub 48 and abut the shoulder 50 to form a vacuumtight seal with the aspirator 30. After use, the suction tubing 52 can be removed and the aspirator 30 discarded, if desired.

The trailing end 54 of the hub 40 defines a female luer coupling 56. The luer coupling 56 is adapted to receive in conventional mating relationship a male luer coupling 58. The male coupling 58 may be a conventional perfusion adaptor connector which is conventionally mounted upon the end of tubing 60. Notably, the versatility that the aspirator 30 has in accommodating instant attachment either to the conventional suction tubing 52 or the perfusion adaptor 58 makes two-way fluid communication through the aspirator 30 possible.

In the use of the aspirator 30, suction tubing 52 is connected to the hub 48 and suction imposed at the leading end 32 through passageway 43. Either before or after the suction is imposed, the leading end 32 is caused to penetrate the aorta between the aortic valve ring (not shown) and the innominate artery takeoff 26. The highest point of the aorta is generally preferred inasmuch as it is probable that any air emboli will be trapped there.

The entire length of the leading end 32 is penetrated into the aorta, the shoulder 44 preventing the bevel 36 from inadvertently penetrating the underside of the aorta. Because of the peripherally spaced apertures 38, any air emboli in the area will be immediately aspirated through the hollow 34 of the needle and along the passageway 43 away from the heart. Significantly, the weight of the suction tubing 52 naturally causes the tube 52 to lie along the top of the aorta and along the upper exposed portion of the heart. Because of the bend 42 in the shank 40, this natural tendency of the tube 52 to repose flat serves to hold the leading end 32 in the most effective position for aspirating blood. Moreover, intentional or inadvertent lateral movement of the tube 52 will not lacerate or otherwise injure adjacent portions of the aorta. Rather, the leading end 32 may be rotated about its longitudinal axis without serious injury to the aorta. It is also observed that suturing the aspirator 30 in place upon the aorta 24 is not necessary because the natural weight of the tube 52 and the configuration of the shank 40 and tip 32 tend to hold the aspirator in operable position. The aspirator 30 is removed easily by lifting the leading end 32 vertically away from the aorta 24.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

what is claimed and desired to be secured by the U.S. Letters Patent is:

1. An air embolus aspirator comprising:

a hollow cannula having a sharpened tip for penetrating a blood vessel and a length less than the diameter of the blood vessel so that the full length of the cannula may be embedded in the blood vessel without damaging the underside of the blood vessel, the cannula presenting means for admitting air into the hollow of the cannula comprising radially spaced, elongated slots in the cannula, said admitting means spanning a plurality of radially spaced locations along the surface of the cannula;

a hollow shank having an annularly enlarged shoulder at a first end of the hollow shank, the hollow shank being mounted upon the cannula at the shoulder, the shoulder limiting the distance of penetration of the cannula, the hollow shank forming an angle of about 90° to the cannula at the shoulder so that the hollow shank will repose essentially flat against the penetrated surface while the cannula is projected transverse to the path of blood flow in the blood vessel thereby permitting rotation of said cannula about its longitudinal axis, the hollow of the shank communicating with the interior of the cannula and the shank defining an angular fluid path of about 90° between the cannula and the hollow shank; and a hub mounted upon the shank and comprising means for coupling the aspirator to a source of reduced pressure to thereby aspirate away any air embolus in the vicinity of the cannula.

2. An air embolus aspirator as defined in claim 1 wherein said admitting means comprises a spirally oriented slot.

3. An air embolus aspirator as defined in claim 1 wherein said hub comprises a female coupling comprising an inwardly tapered coupling socket.

4. An air embolus aspirator as defined in claim 1 wherein said hub is diametrally reduced to receive conventional suction tubing in telescopic relation.

5. An air embolus aspirator comprising:

a cannula comprising a beveled leading tip and a plurality of radially spaced apertures therein, the apertures being elongated in the direction parallel to the axis of the cannula, the cannula terminating in an annularly enlarged shoulder at a base, the shoulder tapering rearwardly and limiting penetration of the cannula;

a plastic intermediate portion, mounted upon the cannula at the shoulder, said intermediate portion being bent at the shoulder to about 90° with respect to the axis of the cannula so that the intermediate portion may repose essentially flat over a blood vessel upon penetration of the cannula into the blood vessel thereby permitting rotation of said cannula about its axis;

a hub comprising a female fitting mounted upon the trailing end of the intermediate portion; and means coupling the hub to aspirating means for physically aspirating the air from the blood vessel.

* * * * *